(12) United States Patent
Kato et al.

(10) Patent No.: US 8,512,536 B2
(45) Date of Patent: Aug. 20, 2013

(54) NOX SENSOR AND PRODUCTION METHOD THEREOF

(75) Inventors: Kenji Kato, Nagoya (JP); Hisashi Sasaki, Konan (JP); Koji Shiotani, Kusugai (JP)

(73) Assignee: NGK Spark Plug Co., Ltd., Aichi (JP)

( * ) Notice: Subject to any disclaimer, the term of this patent is extended or adjusted under 35 U.S.C. 154(b) by 1203 days.

(21) Appl. No.: 12/358,678

(22) Filed: Jan. 23, 2009

(65) Prior Publication Data
US 2009/0188813 A1 Jul. 30, 2009

(30) Foreign Application Priority Data

Jan. 24, 2008 (JP) ................................. 2008-013227

(51) Int. Cl.
*G01N 27/407* (2006.01)
*G01N 27/409* (2006.01)
*G01N 27/41* (2006.01)

(52) U.S. Cl.
USPC ........ 204/424; 204/430; 204/431; 205/784.5; 205/780.5; 205/781

(58) Field of Classification Search
USPC ..................... 204/400–435; 205/775–794.5; 123/672–703; 73/23.31, 23.32
See application file for complete search history.

(56) References Cited

U.S. PATENT DOCUMENTS

| 4,747,930 A * | 5/1988 | Kojima et al. ................. 204/412 |
| 5,942,190 A | 8/1999 | Kato et al. |
| 6,214,207 B1 | 4/2001 | Miyata et al. |
| 6,562,212 B2 * | 5/2003 | Katafuchi et al. ............. 204/427 |
| 2007/0276580 A1 * | 11/2007 | Toda et al. ..................... 701/108 |

FOREIGN PATENT DOCUMENTS

| JP | 05-018938 A | 1/1993 |
| JP | 09-288085 A | 11/1997 |
| JP | 10-142194 A | 5/1998 |
| JP | 11-304758 A | 11/1999 |
| JP | 2004-294079 A | 10/2004 |

OTHER PUBLICATIONS

Minej et al., JP2004294079(A) machine translation.*

* cited by examiner

*Primary Examiner* — Keith Hendricks
*Assistant Examiner* — Susan D Leong
(74) *Attorney, Agent, or Firm* — Sughrue Mion, PLLC

(57) ABSTRACT

A NOx sensor includes a sensor element equipped with first and second pumping cells to define first and second measurement chambers. The first pumping cell exerts an oxygen pumping action against the first measurement chamber to adjust the oxygen concentration in the gas under measurement within the first measurement chamber to a given level. The second pumping cell exerts an oxygen pumping action against the second measurement chamber to produce a pumping cell current according to the NOx concentration in the gas under measurement. When the moisture content of the gas under measurement changes from 2 vol % to 8 vol %, the NOx sensor allows a variation of NOx concentration detection value based on the pumping cell current in such a manner that the NOx concentration detection value reaches a transient peak value of 20 ppm or smaller and converges to ±5 ppm of a reference value within 5 seconds.

8 Claims, 3 Drawing Sheets

NOX SENSOR AND PRODUCTION METHOD THEREOF

BACKGROUND OF THE INVENTION

The present invention relates to a NOx sensor for detecting the concentration of nitrogen oxides (NOx) in gas under measurement, such as combustion gas or exhaust gas of an internal combustion engine or combustor, and a production method thereof. Hereinafter, the term "front" refers to a gas sensing side with respect to the axial direction of a NOx sensor and the term "rear" refers to a side opposite to the front side.

In response to the recent tightened automotive emission regulations, there arises a demand to reduce NOx in engine exhaust gases. On this purpose, NOx sensors have been developed for direct measurements of NOx concentrations in the exhaust gases.

The NOx sensor generally includes a sensor element equipped with first and second pumping cells, each of which has an oxygen ion conducting solid electrolyte material and a pair of electrodes arranged on the solid electrolyte material, to define a first measurement chamber in communication with the sensor outside and a second measurement chamber in communication with the first measurement cell. When the exhaust gas is introduced as gas under measurement into the first measurement chamber, the first pumping cell effects its oxygen pumping action against the first measurement cell so as to adjust the oxygen concentration of the gas under measurement in the first measurement chamber to a given level. When the gas under measurement is introduced from the first measurement chamber into the second measurement chamber, the second pumping cell decomposes NOx in the gas under measurement and performs its oxygen pumping action against the second measurement chamber so as to produce an electric current as the result of pumping of $O_2$ dissociated from the NOx in the gas under measurement. The NOx concentration of the gas under measurement can be thus determined based on the second pumping cell current.

However, the NOx sensor (sensor element) cannot obtain adequate sensor characteristics due to insufficient electrode activity just by arranging the electrodes on the solid electrolyte material. In order to attain adequate sensor characteristics, Japanese Laid-Open Patent Publication No. 5-18938 proposes performing aging treatment on the NOx sensor element under a high-temperature atmosphere with the application of a voltage between the cell electrodes. Further, Japanese Laid-Open Patent Publication No. 2004-294079 proposes performing aging treatment on the sensor element under a high-temperature atmosphere and then under a lean atmosphere so as to prevent initial fluctuations in sensor characteristics due to excessive electrode activity.

SUMMARY OF THE INVENTION

When the moisture content of the gas under measurement changes suddenly e.g. upon shifting of the engine from an idling state into a drive state, there arises a transient peak in the second pumping cell current that causes a variation of the detection value of the NOx sensor. This results in a deterioration of NOx concentration detection accuracy.

It is accordingly an object of the present invention to provide a NOx sensor capable of detecting the concentration of NOx in gas under measurement accurately even when the moisture content of the gas under measurement changes suddenly. It is also an object of the present invention to provide a production method of the NOx sensor.

According to one aspect of the present invention, there is provided a NOx sensor comprising a sensor element equipped with first and second pumping cells to define first and second measurement chambers so that gas under measurement first flows into the first measurement chamber and then from the first measurement chamber into the second measurement chamber, the first pumping cell being capable of exerting an oxygen pumping action against the first measurement chamber to adjust the concentration of oxygen in the as under measurement in the first measurement chamber to a given level, the second pumping cell being capable of exerting an oxygen pumping action against the second measurement chamber to produce a pumping cell current in accordance with the concentration of NOx in the gas under measurement, wherein, when the moisture content of the gas under measurement changes from 2 vol % to 8 vol %, the NOx sensor allows a variation of a NOx concentration detection value based on the pumping cell current in such a manner that the NOx concentration detection value reaches a transient peak value of 20 ppm or smaller and converges to ±5 ppm of a reference value within 5 seconds.

According to another aspect of the present invention, there is provided a production method of a NOx sensors the NOx sensor having a sensor element equipped with first and second pumping cells to define first and second measurement chambers so that gas under measurement first flows into the first measurement chamber and then from the first measurement chamber into the second measurement chamber, the first pumping cell being capable of exerting an oxygen pumping action against the first measurement chamber to adjust the oxygen concentration of the gas under measurement in the first measurement chamber to a given level, the second pumping cell being capable of exerting an oxygen pumping action against the second measurement chamber to produce a pumping cell current in accordance with the NOx concentration of the gas under measurement and having a solid electrolyte material, a first electrode arranged on the solid electrolyte material at a position inside the second measurement chamber and a second electrode arranged on the solid electrolyte material at a position outside the second measurement chamber, the production method comprising: subjecting the sensor element to aging in a rich atmosphere of substantially constant moisture content at a given temperature range through the application of a voltage between the first and second electrodes.

The other objects and features of the present invention will also become understood from the following description.

DESCRIPTION OF THE EMBODIMENTS

The present invention will be described in detail below with reference to the drawings.

Figure 1:
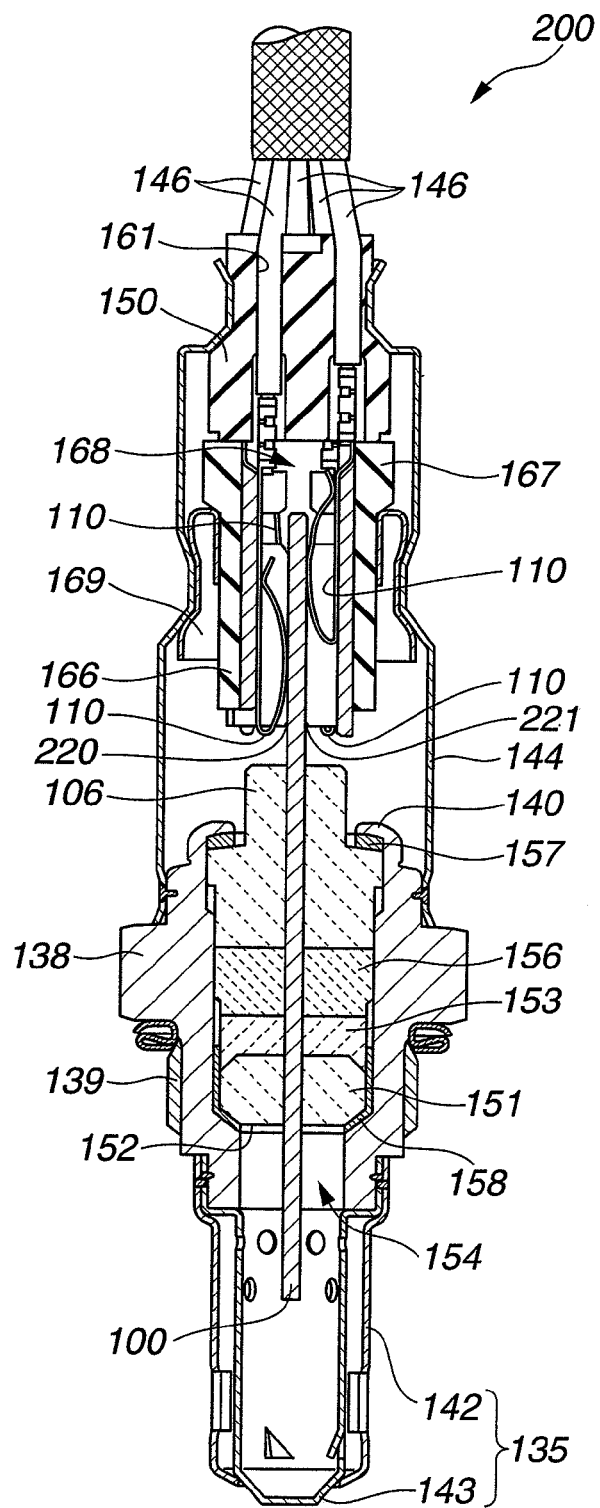
FIG. 1 is a sectional view of a NOx sensor according to one embodiment of the present invention.

Referring to FIG. 1, a NOx sensor 200 for an automotive internal combustion engine according to one exemplary embodiment of the present invention includes a cylindrical metal shell 138, a plate-shaped sensor element 100, a cylindrical ceramic sleeve 106, an annular ceramic holder 151, talc rings 153 and 156 (as packed powder layers), a swage ring 157, a cylindrical metal holder 158, front and rear outer covers 135 and 144, a grommet 150, a cylindrical insulating contact member 166, six connection terminals 110, six lead wires 146 and a retaining member 169. It is noted that only two of the six connection terminals 110 and three of the six lead wires 146 awe shown in FIG. 1 for ease of illustration.

The metal shell 138 has a through hole 154 extending along the axial direction of the NOx sensor 200. A threaded portion 139 for mounting the NOx sensor 200 on an exhaust passage of the engine is formed on an outer circumferential surface of the metal shell 138. A stepped portion 152 is formed on inner circumferential surface of the metal shell 138 so as to protrude radially outwardly and have a conically tapered surface at a given angle with respect to a horizontal plane orthogonal to the axial direction of the NOx sensor 200.

The sensor element 100 is inserted in the through hole 154 of the metal shell 138, with front and rear end portions of the sensor element 100 protruding from front and rear ends of the metal shell 138, respectively. Two terminal areas 220 and 221 are formed on the rear end portion of the sensor element 100.

The ceramic holder 151, the talc rings 153 and 156 and the ceramic sleeve 106 are arranged, in order of mention from the front side to the rear side, around a middle portion of the sensor element 100 and within the through hole 154 of the metal shell 138. The swage ring 157 is disposed between the ceramic sleeve 106 and the rear end 140 of the metal shell 138 so as to swage the rear end 140 of the metal shell 138 on the ceramic sleeve 106 via the swage ring 157 and thereby press the ceramic sleeve 106 toward the front side. Further, the metal holder 158 is fitted on the ceramic holder 151 and the talc ring 153 and seated on the stepped portion 152 of the metal shell 138 so as to hermetically retain the sensor element 100 together with the ceramic holder 151 and the talc ring 153.

The front outer cover 135 is attached by e.g. welding to the front end of the metal shell 138 and accommodates therein the protruding front end portion of the sensor element 100. In the present embodiment, the front outer protector 135 has a double structure of outer and inner cover members 142 and 143. The outer and inner cover members 142 and 143 are made of metal material such as stainless steel. A plurality of holes are formed in the cover members 142 and 143 for supply and drain of gas under measurement.

The rear outer cover 144 is attached to the rear end of the metal shell 138 and accommodates therein the protruding rear end portion of the sensor element 100.

The grommet 150 is formed with a lead wire insertion hole 161 and fitted in a rear opening of the outer cover 144. The lead wires 146 are inserted through the lead wire insertion hole 161 of the grommet 150 and electrically connected to the terminal areas 220 and 221 of the rear end portion of the sensor element 100 via the connection terminals 110.

The insulating contact member 166 has a terminal insertion hole 168 extending along the axial direction of the NOx sensor 200 and surrounds therein the terminal areas 220 and 221 of the rear end portion of the sensor element 100, with the connection terminals 110 disposed between the sensor element 100 and the contact member 166. A radially outwardly protruding flange portion 167 is formed on an outer circumferential surface of the contact member 166 so as to retain thereon the contact member 166 in the outer cover 144 by engagement of the flange portion 167 on the outer protector 144 via the retaining member 169.

Figure 2:
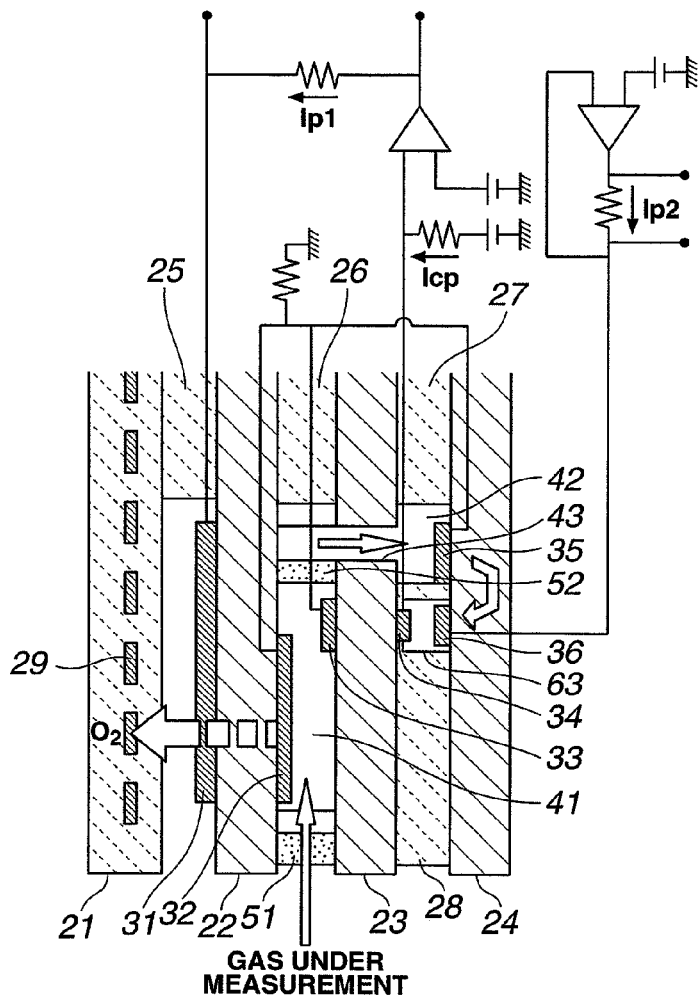
FIG. 2 is a sectional view of a sensor element of the NOx sensor according to one embodiment of the present inventions.

Referring to FIG. 2, the sensor element 100 has a multilayer structure in which a first solid electrolyte layer 22, an insulating layer 26, a second solid electrolyte layer 23, an insulating layer 27 (28) and a third solid electrolyte layer 24 are laminated together in order of mention. In the present embodiment, the solid electrolyte layers 22, 23 and 24 are predominantly composed of oxygen ion conducting zirconia whereas the insulating layers 26, 27 and 28 are predominantly formed of alumina. A front end portion of the insulating layer 26 is cut away in a U-shaped curve to define a first measurement chamber 41 between the first and second solid electrolyte layers 22 and 23. An opening 43 is formed in the solid electrolyte layer 23 to define a second measurement chamber 42 between the first and third solid electrolyte layers 22 and 24 and between the insulating layers 27 and 28. Further, an opening is formed in the insulating layer 28 to define a reference oxygen chamber 63 between the second and third solid electrolyte layers 23 and 24. The reference oxygen chamber 63 is filled with a porous material. The sensor element 100 also has first and second diffusion rate control members 51 and 52 made of porous material such as alumina and porous electrodes 31 to 36 made of conductive material such as platinum.

The first diffusion rate control member 51 is arranged on a front end of the first measurement chamber 41 so that the first measurement chamber 41 is in communication with the sensor outside via the first diffusion rate control member 51. The second diffusion rate control member 52 is arranged on a rear end of the first measurement chamber 41 (as a partition between the first and second measurement chambers 41 and 42 so that the second measurement chamber 42 is in communication with the first measurement chamber 41 via the second diffusion rate control member 52. With such an arrangement, the gas under measurement is first introduced into the first measurement chamber 41 through the first diffusion rate control member 51 and then into the second measurement chamber 42 through the second diffusion rate control member 52.

The porous electrodes 32 and 31 are located on opposite sides of the first solid electrolyte layer 22 at positions inside and outside the first measurement chamber 41, respectively. As the solid electrolyte layer 22 allows oxygen ion conduction therethrough between the sensor outside (engine exhaust passage) and the first measurement chamber 41 by the passage of an electric current between the porous electrodes 31 and 32, the solid electrolyte layer 22 and the porous electrodes 31 and 32 function together as a first pumping cell that effects an oxygen pumping action against the first measurement chamber 41. For purposes of illustration, the porous electrodes 32 and 31 are hereinafter referred to as "working electrode" and "counter electrode", respectively.

The porous electrodes 33 and 34 are located on opposite sides of the second solid electrolyte layer 23 at positions inside the first measurement cell 41 and the reference oxygen chamber 63. As the solid electrolyte layer 23 pumps oxygen from the first measurement chamber 41 into the reference oxygen chamber 63 as reference oxygen by the passage of a weak electric current between the porous electrodes 33 and 34, the solid electrolyte layer 23 and the porous electrodes 33 and 34 function together as an oxygen concentration measurement cell. The porous electrodes 33 and 34 are hereinafter referred to as "sensing electrode" and "reference electrode", respectively, for purposes of illustration. As is seen in FIG. 2, the sensing electrode 33 of the oxygen concentration measurement cell is positioned on a downstream side of the working electrode 32 of the first pumping cell with respect to the direction of flow of the gas under measurement in the first measurement chamber 41.

The porous electrodes 35 and 36 are located on a side of the third solid electrolyte layer 24 facing the second solid electrolyte layer 23 at positions inside and outside the second measurement chamber 42 (i.e. at positions inside the second measurement chamber 42 and the reference oxygen chamber 63). As the solid electrolyte layer 24 allows oxygen ion conduction therethrough from the second measurement chamber 42 to the reference oxygen chamber 63 by the application of a voltage between the porous electrodes 35 and 36, the solid electrolyte layer 24 and the porous electrodes 35 and 36 function together as a second pumping cell that effects an oxygen pumping action against the second measurement chamber 42. The porous electrodes 35 and 36 are hereinafter referred to as "working electrode" and "counter electrode", respectively, for purposes of illustration.

Referring again to FIG. 2, the sensor element 100 further has a heater 29 for activating the sensor element 100 by heating so as to enhance the oxygen ion conductivity of the solid electrolyte layers 22, 23 and 24 and thereby stabilize the sensor element 100. The heater 29 is made of platinum and embedded in an insulating layer 21 along the longitudinal direction of the sensor element 100. The insulating layer 21 is made of alumina and laminated by a lamination cement 25 onto a side of the solid electrolyte layer 22 opposite from the insulating layer 26, with a space left between the insulating layer 21 and the solid electrolyte layer 22.

The above-structured NOx sensor 200 operates as follows.

Upon the energization of the heater 29, the heater 29 heats the first pumping cell, the oxygen concentration measurement cell and the second pumping cell to an activation temperature of e.g. 550° C. or higher.

When engine exhaust gas is introduced as the gas under measurement into the first measurement chamber 41 through the first diffusion rate control member 51, the first pumping cell exerts its oxygen pumping action to pump $O_2$ in and out of the first measurement chamber 41 by the passage of a first pumping cell current Ip1. At this time, the first pumping cell current Ip1 is regulated in such a manner as to maintain a constant voltage of e.g. 425 mV between the working and counter electrodes 32 and 31 and thereby adjust the oxygen concentration of the gas under measurement in the first measurement chamber 41 to a given level (corresponding to the control voltage of the oxygen concentration measurement cell) without causing decomposition of NOx in the first measurement chamber 41.

After the oxygen concentration of the gas under measurement in the first measurement chamber 41 is adjusted to the given level, the gas under measurement is introduced from the first measurement chamber 41 into the second measurement chamber 42 through the second diffusion rate control member 52. Upon contact of the gas under measurement with the second pumping cell, the second pumping cell decomposes NOx in the gas under measurement to $N_2$ and $O_2$ under the catalysis of the working electrode 35 with the application of a constant voltage of e.g. 450 mV (higher than the control voltage of the oxygen concentration measurement cell) between the working and counter electrodes 35 and 36. The second pumping cell then exerts its oxygen pumping action to pump the resulting $O_2$ from the second measurement chamber 142 into the reference oxygen chamber 63 and produce a second pumping cell current Ip2 therethrough as the result of pumping of the $O_2$ dissociated from the NOx in the gas under measurement.

As the second pumping cell current Ip2 is linearly proportional to the NOx concentration of die gas under measurement, the NOx concentration of the gas under measurement can be determined based on the second pumping cell current Ip2. In the present embodiment, the NOx sensor 200 calculates a NOx concentration value (more specifically, a NO concentration value) from the second pumping cell current Ip2.

Although not shown in the drawings, a sensor control unit is provided with a microcomputer and connected with the sensor element 100 so as to convert the second pumping cell current Ip2 to a voltage, calculate the NOx concentration detection value from the voltage and output the NOx concentration detection value to an engine control unit for engine feedback control. There is no particular restriction on the NOx concentration calculation process. For example, the NOx concentration detection value can be calculated by the microcomputer according to the process disclosed in Japanese Laid-Open Patent Publication No. 11-304758, Japanese Laid-Open Patent Publication No. 10-142194 and U.S. Pat. No. 6,214,207, which are hereby incorporated by reference. A detailed explanation of the NOx concentration calculation process will be thus omitted therefrom. Namely, the NOx concentration detection value can be obtained from the CAN output of the microcomputer. Alternatively, the engine control unit may read the output from the sensor element 100 or sensor control unit (microcomputer) and calculate the NOx concentration value based on the read sensor output. As another alternative, the NOx concentration detection value may be calculated using as a reference a value of the second pumping cell current Ip2 in a state of the NOx sensor 200 being subjected to gas of known NOx concentration.

In the above-structured NOx sensor 200, there arises a transient flow of the second pumping cell current Ip2 in response to a change (sudden change) in moisture content of the gas under measurement even in the absence of NOx in the gas under measurement. As the NOx concentration detection value is calculated from the second pumping cell current Ip2 as mentioned above, such a transient peak of the second pumping cell current Ip2 leads to a variation of the NOx concentration detection value. The influence of the transient peak on the NOx concentration detection value becomes larger as the magnitude (maximum peak value) of the transient peak increases. In addition, the time during which the transient peak affects the NOx concentration detection value becomes increased as it takes a longer time from the change of the gas moisture content until when the NOx concentration detection value converges to a reference value.

Figure 3:
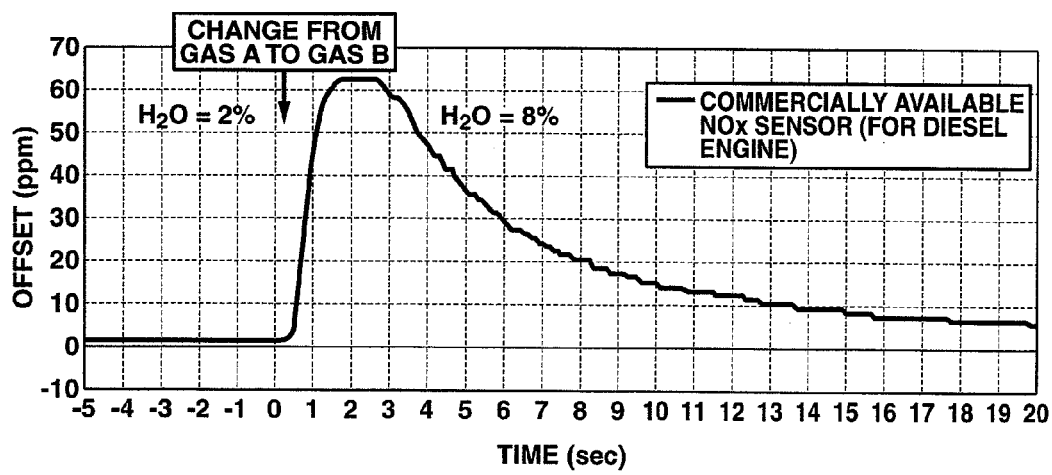
FIG. 3 is a graph showing a transient peak (offset) in the detection value of a commercially available conventional NOx sensor in the case where the moisture content of gas under measurement changes from 2 vol % to 8 vol %.

For example, the detection value (offset value) of a commercially available conventional NOx sensor for use in a diesel vehicle reaches a large transient peak value of 60 ppm due to a transient peak in pumping cell current as shown in FIG. 3 when the moisture content of gas under measurement changes from 2 vol % to 8 vol %. It takes several ten seconds from the change of the gas moisture content from 2 vol % to 8 vol % until when the detection value converges to its original, reference value (0 ppm). In this way, the NOx concentration detection accuracy of the conventional NOx sensor becomes deteriorated when the moisture content of the gas under measurement changes suddenly e.g. during driving.

Accordingly, the NOx sensor 200 is so configured as to, when the moisture content of the gas under measurement changes from 2 vol % to 8 vol %, allow a variation of the NOx concentration detection value in such a manner that the NOx concentration detection value reaches a transient peak value of 20 ppm or smaller and converges to ±5 ppm of a reference value within 5 seconds of the time of change of the gas moisture content in the present embodiment. It is herein defined that, when the moisture content of the gas under measurement changes from 2 vol % to 8 vol %, the percentage amount of moisture ($H_2O$) in the gas under measurement instantly increases from 2 vol % to 8 vol % without causing any change in the percentage amount of each of any gas component or components other than the moisture ($H_2O$). Further, the reference value is defined as the original value of the second pumping cell current Ip2 before the change of the gas moisture content, i.e., the value of the second pumping cell Ip2 in a steady state where there is no change of gas moisture content.

When the moisture content of the gas under measurement changes, there arises a variation of the NOx concentration detection value of the NOx sensor 200 due to a transient flow of the second pumping cell current Ip2. In the above configuration, however, such a variation of the NOx concentration detection value can be limited to a lower degree so that the NOx concentration detection value reaches a lower transient peak value and converges quickly to its reference value. It is therefore possible to prevent the detection accuracy of the NOx sensor 200 from being deteriorated even when the moisture content of the gas under measurement changes.

It is particularly desirable that the NOx concentration detection value converges to ±10 ppm of the reference value within 3 seconds of the change of the gas moisture content. In this case, it is possible to prevent the detection accuracy deterioration of the NOx sensor 200 more effectively as the NOx concentration detection value converges more quickly.

The above-specified transient peak characteristics of the NOx sensor 200 can be obtained easily and efficiently by subjecting the sensor element 100, notably the second pumping cell working electrode 35, to aging in a rich atmosphere of substantially constant moisture content through the application of a voltage between the second pumping cell working and counter electrodes 35 and 36 while heating the sensor element 100 (second pumping cell working electrode 35) to a given temperature range. The rich atmosphere is herein defined as an atmosphere having a lower oxygen content (oxygen partial pressure) than that corresponding to a stoichiometric air-fuel ratio ($\lambda=1$) for ideal complete combustion. It is also defined that the amount of change in absolute humidity per hour is 8% or less when the moisture content of the rich atmosphere is substantially constant. By the above aging treatment, it is possible to decrease and limit the variation of the NOx concentration detection value and thereby prevent the detection accuracy deterioration of the NOx sensor 200 even when the moisture content of the gas under measurement changes. It is not clear why the variation of the NOx concentration detection value can be limited by the aging treatment but is estimated that the surface of the second pumping cell working electrode 35 becomes porous through the aging treatment, which contributes to a decrease in the transient peak magnitude of the second pumping cell current Ip2 in response to the gas moisture change.

Specific examples of the rich atmosphere of the aging treatment are an atmosphere of gas containing several vol % $H_2$, more than 0 to 5 vol % or less $H_2O$ (moisture) and the balance being $N_2$ and an atmosphere of gas containing 1 vol % CO, 10 vol % $CO_2$, more than 0 to 5 vol % or less $H_2O$ (moisture) and the balance being $N_2$. The temperature of the second pumping cell during the aging treatment is set to e.g. 550 to 700° C. The voltage applied between the working and counter electrodes 35 and 36 during the aging treatment is set to e.g. over 0 to 1.8 V or lower. The time of the aging treatment is set to e.g. about 60 seconds. In order to enhance the effect of the aging treatment, it is preferable that the voltage applied between the working and counter electrodes 35 and 36 during the aging treatment is an AC voltage varying between two discrete amplitudes (e.g. between the ON-voltage level of 0 to 1.8 V and the OFF-voltage level of 0 V) at given periodicity. It is particularly preferable to perform the aging treatment under the conditions that: the AC voltage between the working and counter electrodes 35 and 36 ranges from 1.0 to 1.8 V; the moisture content of the aging atmosphere ranges from 0.1 to 1 vol. %; and the temperature of the second pumping cell ranges from 600 to 700° C.

The aging treatment can be performed on the sensor element 100 before the process of assembling the sensor element 100 into the NOx sensor 200 or after the process of assembling the sensor element 100 into the NOx sensor 200 (in finished or semi-finished form). Further, the aging treatment can be performed using the built-in heater 29 of the sensor element 100 or any other external heater.

In order to stabilize the output of the second pumping cell current Ip2, additional aging treatment may be performed by driving the NOx sensor 200 (sensor element 100) in a normal manner in an air atmosphere for a predetermined time period.

The application of the NOx sensor 200 is not limited to the above. The NOx sensor 200 can be used not only to detect the NOx concentration of exhaust gas of the automotive internal combustion engine, but also to detect the NOx concentration of combustion gas of the automotive internal combustion engine or any other combustor such as boiler.

The present invention will be described in more detail by reference to the following examples. It should be however noted that the following examples are only illustrative and not intended to limit the invention thereto.

Test samples of the NOx sensor 200 (as Examples 1 to 3) were produced and subjected to aging. The aging was performed on each test sample by heating the second pumping cell in a rich atmosphere containing 3 vol % $H_2$, 0.5 vol % $H_2O$ and the balance being $N_2$ with the application of an AC voltage of 0V/1.6V between the second pumping cell working and counter electrodes 35 and 36. In Examples 1 to 3, the aging temperature was set to different levels ranging from 630 to 700° C. A test sample of NOx sensor (as Comparative Example) was produced in the same manner as above, except that the test sample was not subjected to aging.

Figure 4:
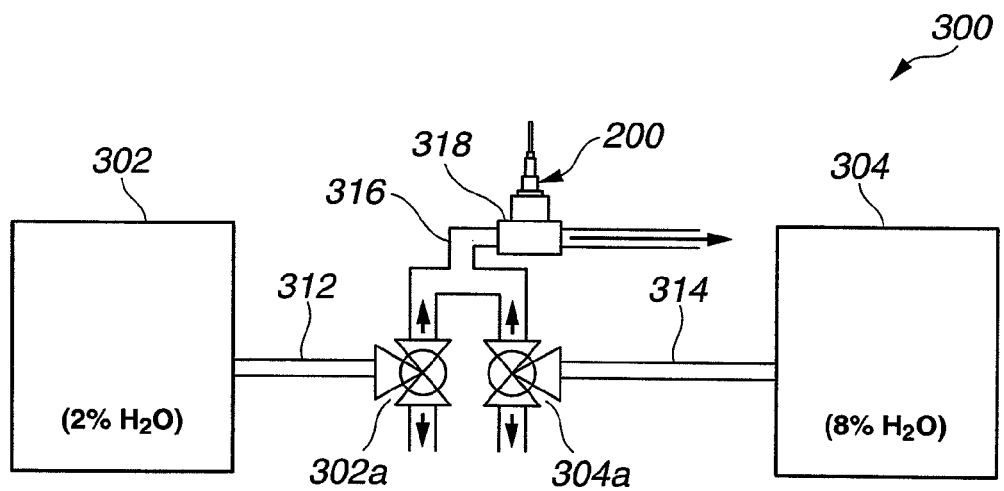
FIG. 4 is a schematic view of an offset measurement piping system for the NOx sensor according to one embodiment of the present invention.
Figure 5:
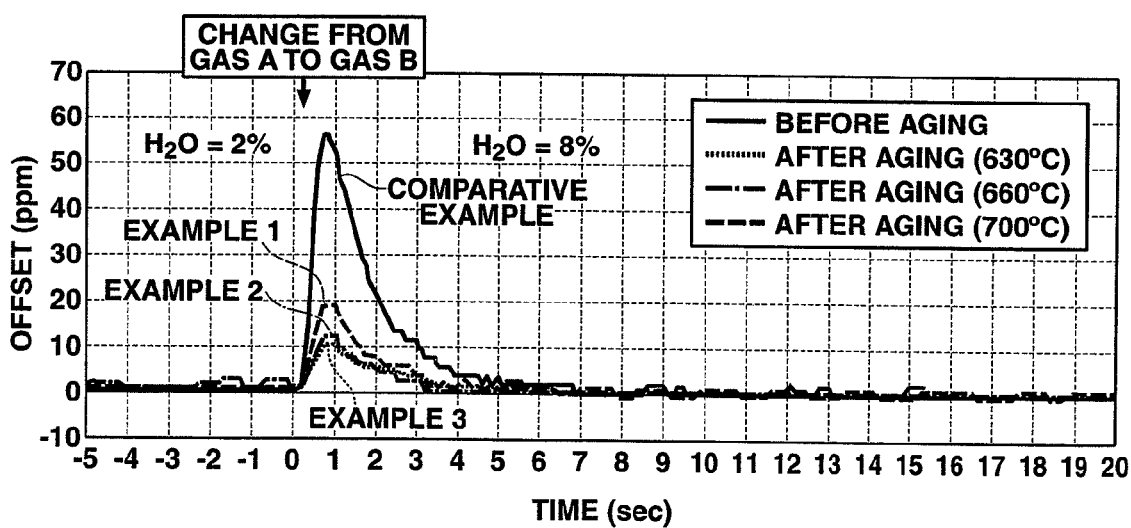
FIG. 5 is a graph showing a transient peak (offset) in the detection value of the NOx sensor according to one embodiment of the present invention in the case where the moisture content of gas under measurement changes from 2 vol % to 8 vol %.

After the aging, offset measurement test was carried out on each of the test samples by the following procedure using an offset measurement system 300 shown in FIG. 4. The offset measurement system 300 had a gas generation unit 302 capable of generating test gas A, a gas generation unit 304 capable of generating test gas B different in moisture content from the test gas A, gas valves 302a and 304a connected to the gas generation units 302 and 304 via gas pipes 312 and 314 to supply therethrough the test gas A and test gas B, respectively, and an integrated gas pipe 316 connected to the gas valves 302a and 304a and formed with a branch portion 318 to mount thereon the test sample and subject the test sample to the test gas A, B. Pure $N_2$ with a moisture content of 2 vol % was used as the test gas A and pure $N_2$ with a moisture content of 8 vol % was used as the test gas B. The $O_2$ content, $CO_2$ content, NO concentration of the test gas A, B were controlled to 0 vol %, 0 vol % and 0 ppm, respectively. The temperature of the test gas A, B was set to room temperature. The output (second pumping cell current Ip2) of the test sample was converted into a NOx concentration detection value (offset value) by the microcomputer of the sensor control unit. Herein, the offset value of the test sample in a steady state where there was no change in gas moisture content was set to 0 ppm. In the present offset measurement test, the test gas A was first supplied to the test sample at a rate of 4 m/s by opening the gas valve 302a and closing the gas valve 304a. Under the condition that the test sample was subjected to the test gas A, the offset value of the test sample was measured in real time. Next, the test gas B was supplied to the test sample at a rate of 4 m/s by closing the gas valve 302a and opening the gas valve 304a. The inside of the gas pipe 316 was replaced from the test gas A to the test gas B during about 1 second. The offset value of the test sample was then measured in real time under the condition that the test sample was subjected to the test gas B. The measurement results are indicated in FIG. 5.

In Example 1 where the aging was performed at 700° C., the offset value of the test sample reached a peak value of 20 ppm or smaller. In Example 2 where the aging was performed at 660° C., the offset value of the test sample reached a peak value of slightly over 10 ppm. In Example 3 where the aging was performed at 630° C., the offset value of the test sample reached a lowest peak value of less than 10 ppm or less. Further, the offset value of the test sample converged to ±10 ppm within 3 seconds and to ±5 ppm within 5 seconds in each of Examples 1 to 3. In Comparative Example where no aging was performed, by contrast, the offset value reached a transient peak value of much higher than 20 ppm. In the case of the above-mentioned commercially available conventional NOx sensor, the offset value also reached a transient peak value of much over 20 ppm and did not converge to ±5 ppm even after a lapse of 20 seconds. It has been thus shown that, even when the moisture content of the gas under measurement changes from 2 vol % to 8 vol %, the variation of the NOx concentration detection value can be limited such that the NOx concentration detection value reaches a transient peak value of 20 ppm or smaller and converges to ±5 ppm within 5 seconds (±10 ppm within 3 seconds) by aging the sensor element 100 (second pumping cell) in a rich atmosphere of substantially constant moisture content at a given temperature range through the application of a voltage between the working and counter electrodes 35 and 36.

The entire contents of Japanese Patent Application No. 2008-013227 (filed on Jan. 24, 2008) are herein incorporated by reference.

Although the present invention has been described with reference to the above specific embodiment, the invention is not limited to this exemplary embodiment. Various modifications and variations of the embodiment described above will occur to those skilled in the art in light of the above teachings.

The configuration of the sensor element 100 is not limited to the above. The sensor element 100 may have a two-cell configuration with two solid electrolyte layers as discussed in Japanese Laid-Open Patent Publication No. 9-288085 (FIG. 2) although the sensor element 100 has a three-ell configuration with three solid electrolyte layers 22, 23 and 24 in the above embodiment. Although the heater 29 was bonded to the side of the first solid electrolyte layer 22 by the cement 25 in the above embodiment, the heater 29 may be integrally formed on the side of the third solid electrolyte layer 24 by simultaneous sintering without using the cement 25.

The scope of the invention is defined with reference to the following claims.

What is claimed is:

1. A NOx sensor comprising a sensor element equipped with first and second pumping cells to define first and second measurement chambers so that gas under measurement first flows into the first measurement chamber and then from the first measurement chamber into the second measurement chamber, the first pumping cell being capable of exerting an oxygen pumping action against the first measurement chamber to adjust the concentration of oxygen in the gas under measurement in the first measurement chamber to a given level, the second pumping cell being capable of exerting an oxygen pumping action against the second measurement chamber to produce a pumping cell current in accordance with the concentration of NOx in the gas under measurement,
wherein, when the moisture content of the gas under measurement changes from 2 vol % to 8 vol %, the NOx sensor allows a variation of a NOx concentration detection value based on the pumping cell current in such a manner that the NOx concentration detection value reaches a transient peak value of 20 ppm or smaller and converges to ±5 ppm of a reference value within 5 seconds.

2. The NOx sensor according to claim 1, wherein the NOx sensor allows said variation of the NOx concentration detection value in such a manner that the NOx concentration detection value converges to ±10 ppm of the reference value within 3 seconds when the moisture content of the gas under measurement changes from 2 vol % to 8 vol %.

3. The NOx sensor according to claim 1, wherein the second pumping cell comprises a solid electrolyte material, a first electrode arranged on the solid electrolyte material at a position inside the second measurement chamber and a second electrode arranged on the solid electrolyte material at a position outside the second measurement chamber; and wherein the first electrode has been subjected to aging in a rich atmosphere with the application of a voltage between the first and second electrodes.

4. A production method of a NOx sensor, the NOx sensor having a sensor element equipped with first and second pumping cells to define first and second measurement chambers so that gas under measurement first flows into the first measurement chamber and then from the first measurement chamber into the second measurement chamber, the first pumping cell being capable of exerting an oxygen pumping action against the first measurement chamber to adjust the oxygen concentration of the gas under measurement in the first measurement chamber to a given level, the second pumping cell being capable of exerting an oxygen pumping action against the second measurement chamber to produce a pumping cell current in accordance with the NOx concentration of the gas under measurement and having a solid electrolyte material, a first electrode arranged on the solid electrolyte material at a position inside the second measurement chamber and a second electrode arranged on the solid electrolyte material at a position outside the second measurement chamber, the production method comprising:
subjecting the sensor element to aging in a given aging atmosphere at a given temperature range through the application of a voltage between the first and second electrodes,
wherein said given aging atmosphere is a rich atmosphere of substantially constant moisture content; and
wherein said voltage is an alternating voltage that varies between first and second discrete voltage levels at a given periodicity.

5. The production method according to claim 4, wherein said aging was performed under the conditions that the temperature range of the second pumping cell is 550 to 700° C.

and the moisture content of the rich atmosphere is greater than 0 vol % and less than or equal to 5 vol %.

6. The production method according to claim 4, wherein the first voltage level is 0 to 1.8 V and the second voltage level is 0 V.

7. The production method according to claim 6, wherein the first voltage level is 1.0 to 1.8 V and the second voltage level is 0 V.

8. The production method according to claim 6, wherein said aging was performed under the conditions that the temperature range of the second pumping cell is 550 to 700° C. and the moisture content of the rich atmosphere is greater than 0 vol % and less than or equal to 5 vol %.

\* \* \* \* \*